United States Patent
Yazejian

Patent Number: 5,414,518
Date of Patent: May 9, 1995

[54] METHOD AND APPARATUS FOR THE EVALUATION OF REFLECTIVE SURFACES

[75] Inventor: Diran Yazejian, Bloomfield Hills, Mich.

[73] Assignee: Chrysler Corporation, Highland Park, Mich.

[21] Appl. No.: 228,813

[22] Filed: Apr. 18, 1994

Related U.S. Application Data

[63] Continuation-in-part of Ser. No. 926,450, Aug. 10, 1992, abandoned.

[51] Int. Cl.⁶ ................................ G01B 11/24
[52] U.S. Cl. ..................... 356/376; 356/237; 356/445; 356/371
[58] Field of Search .......... 356/237, 239, 371, 376, 356/445, 446, 448, 429–431; 250/562, 571, 572; 362/33, 61, 217, 218, 219, 220, 221–225, 275, 403; 348/125, 128

[56] References Cited

U.S. PATENT DOCUMENTS

| | | | |
|---|---|---|---|
| 3,643,085 | 2/1972 | Duran | 362/225 |
| 3,666,360 | 5/1972 | Mills et al. | 356/237 |
| 4,533,245 | 8/1985 | Love, III | 356/238 |
| 4,629,319 | 12/1986 | Clarke et al. | 356/237 |
| 4,660,561 | 4/1987 | Nielsen | 362/218 |
| 4,792,232 | 12/1988 | Tobe et al. | 356/394 |
| 4,918,321 | 4/1990 | Klenk et al. | 356/445 |
| 4,929,846 | 5/1990 | Mansour | 356/371 |
| 5,001,614 | 3/1991 | Buss | 362/225 |
| 5,060,118 | 10/1991 | Penrod et al. | 362/33 |
| 5,142,648 | 8/1992 | Fitts et al. | 356/446 |
| 5,237,404 | 8/1993 | Tanaka et al. | 356/376 |

FOREIGN PATENT DOCUMENTS

| | | |
|---|---|---|
| 2439988 | 4/1976 | Germany. |
| 0023205 | 2/1984 | Japan. |
| 0073139 | 4/1988 | Japan. |
| 0210806 | 8/1989 | Japan. |
| 0264448 | 10/1993 | Japan. |

*Primary Examiner*—Hoa Q. Pham
*Attorney, Agent, or Firm*—Mark P. Calcaterra

[57] ABSTRACT

A transportable apparatus for evaluating a reflective object comprises a main body portion and a plurality of elongated light sources attached to the main body portion. The elongated light sources are adapted to produce images in the reflective object which will visually reveal flaws in the surface of the reflective object through portions of discontinuous curvature. The apparatus can be easily transported to various positions about the reflective object, thereby facilitating evaluation of a variety of differently oriented portions of the object.

15 Claims, 3 Drawing Sheets

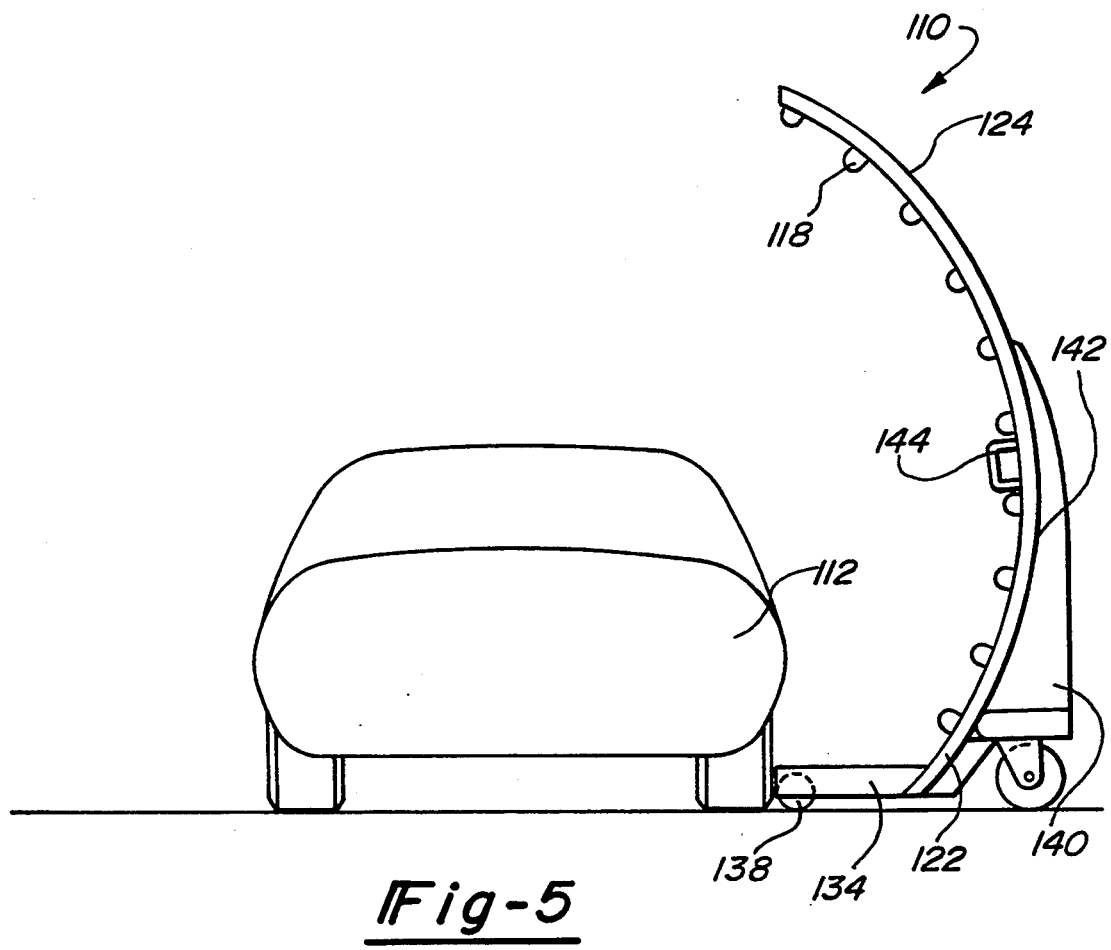
Fig-5
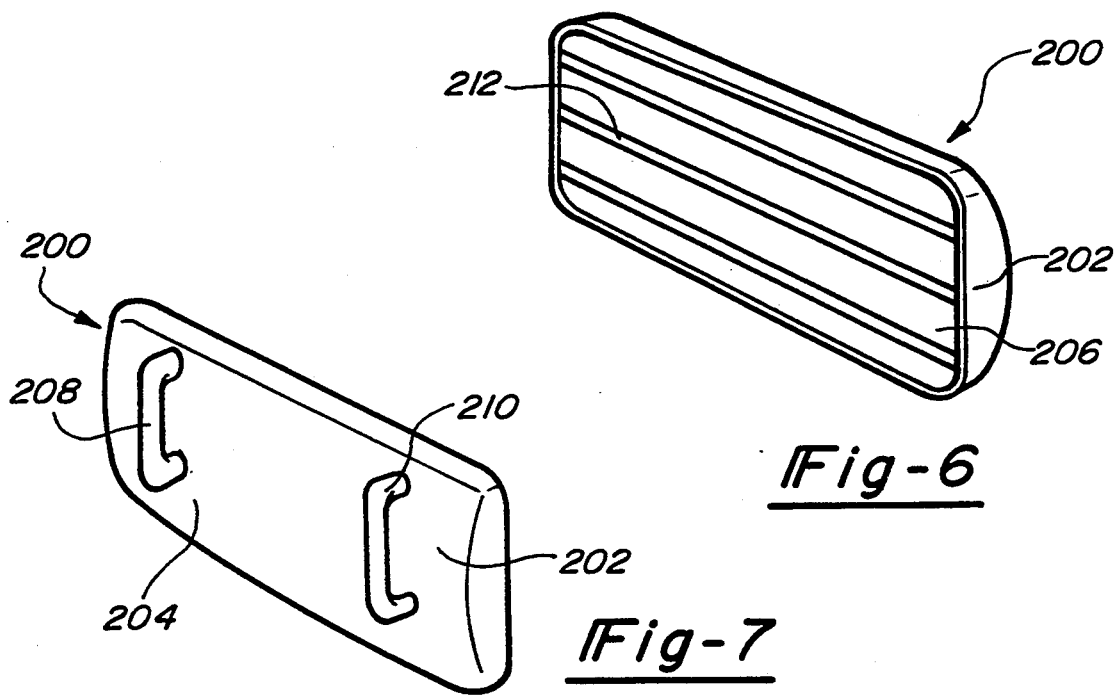
Fig-6
Fig-7

METHOD AND APPARATUS FOR THE EVALUATION OF REFLECTIVE SURFACES

This application is a continuation-in-part of U.S. Ser. No. 07/926,450, filed Aug. 10, 1992 now abandoned.

BACKGROUND OF THE INVENTION

1. Field of the Invention

The present invention relates generally to vehicle design. More particularly, the present invention relates to a method and apparatus for the evaluation of the quality of a reflective surface.

2. Description of Related Art

Following two-dimensional conception of a vehicle design, the design is ultimately embodied in a clay concept model. As is known in the art, the clay concept model is computer-scanned and the surface data is digitized. The digitized surface data which is generated is then analyzed and used to computer mill a verification model. In general, design aspects incorporated in the ultimate panels of the vehicle are intended to be smooth and uninterrupted, thereby creating an aesthetically pleasing appearance. Flawed surfaces are attendant with errors such as low spots, thereby interrupting an otherwise smooth surface.

It is known in the art that analysis of digitized surface data will reveal such flaws in a surface not readily apparent to the eye. However, the digitized data generated from a single clay verification model is voluminous, and analysis of the same is time consuming. Lengthy periods for design are undesirable given the necessity of bringing new vehicle designs to the marketplace before the competition.

It is also known in the art that flaws in a surface often become apparent upon visual inspection when an elongated light source, such as a fluorescent tube, is positioned so as to produce a reflective image in the surface. To accomplish this, the surface must necessarily be reflective. A surface constructed from a substantially light absorbing material, such as clay, can be covered with a reflective material, such as DyNok, commercially available from Minnesota Mining & Manufacturing Co.

In a smooth, unflawed reflective surface, an elongated light source will produce a smooth, gently flowing image. In a flawed surface, the image produced will have portions with discontinuous curvature, resultant from errors such as low spots.

Heretofore, such surface analysis has been typically accomplished by providing a room having a plurality of fluorescent tubes horizontally spaced along at least one wall and at least a portion of the ceiling, often referred to as a "green room". While this type of visual inspection has proven to be an advance in the art, it is not without its inherent limitations. For example, it is necessary to transport the clay verification model to the testing facility. Further, the clay model must continually be maneuvered in order to produce the desired images over the entire vehicle.

SUMMARY OF THE INVENTION

It is an object of the present invention to provide a portable apparatus for evaluating a reflective surface.

It is a further object of the present invention to provide a portable apparatus having a plurality of elongated light sources.

It is still another object of the present invention to provide a portable apparatus for the visual inspection of the surfaces of a vehicle having one portion adapted for inspection of horizontally disposed surfaces and another portion adapted for inspection of vertically disposed surfaces.

The above and other objects are accomplished by providing a portable apparatus for visually inspecting a reflective object. In a first embodiment, the apparatus of the present invention comprises a main body member having a generally linear lower portion and a forwardly curved upper portion. The apparatus further comprises a plurality of elongated fluorescent tubes spaced equally and attached so as to be disposed horizontally to the main body member. When the apparatus is positioned adjacent to a stationary form with a reflective surface, images of the fluorescent tubes are produced in the reflective surface. A quality surface will produce a smooth and aesthetically pleasing reflection pattern of the tubes, while a faulted surface will show erratically spaced and shaped reflections. The faulted surface requires reshaping until the pattern of the reflections are smooth and aesthetically acceptable.

The objects of the present invention are further overcome by a second embodiment in which the apparatus comprises a main body member having forwardly curved upper and lower portions.

Additional objects, advantages, and features of the present invention will become apparent from the following description and appended claims, taken in conjunctions with the accompanying drawings.

BRIEF DESCRIPTION OF THE DRAWINGS

FIG. 5 is a front perspective view of the apparatus of FIG. 4;

FIG. 6 is a front perspective view of a third embodiment of an apparatus incorporating the teachings of the present invention; and FIG. 7 is a rear perspective of the apparatus of FIG. 6.

DETAILED DESCRIPTION OF THE PREFERRED EMBODIMENTS

Figure 1:
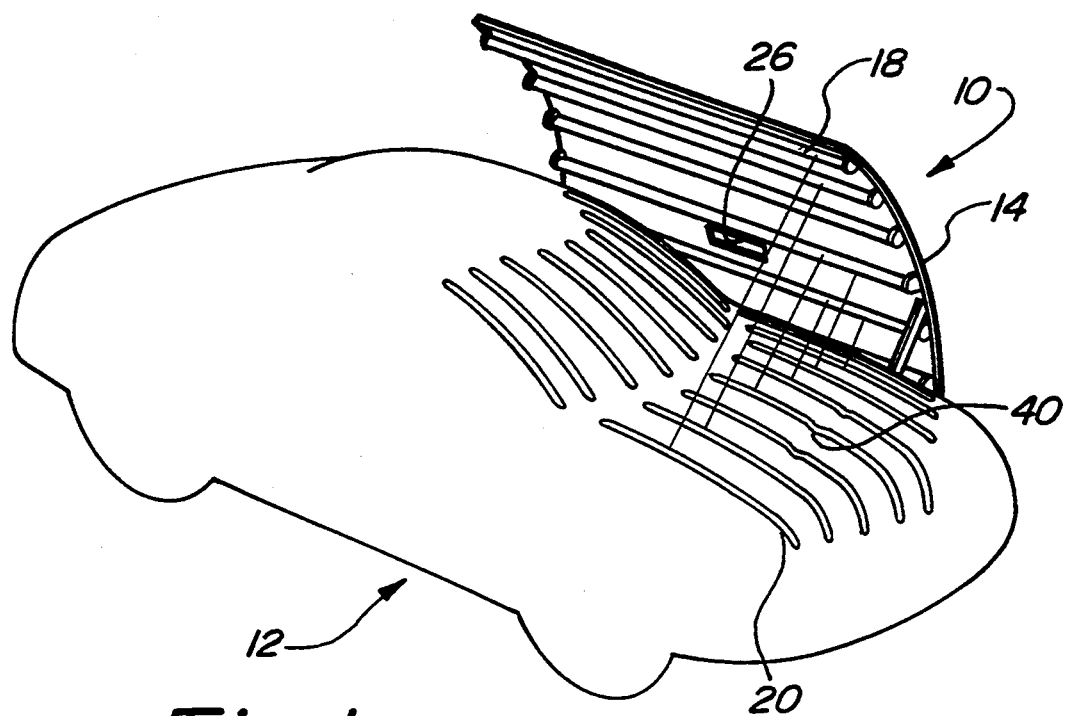
FIG. 1 is a front perspective view of a first embodiment of an apparatus incorporating the teachings of the present invention, shown in operative association with a vehicle model.
Figure 2:
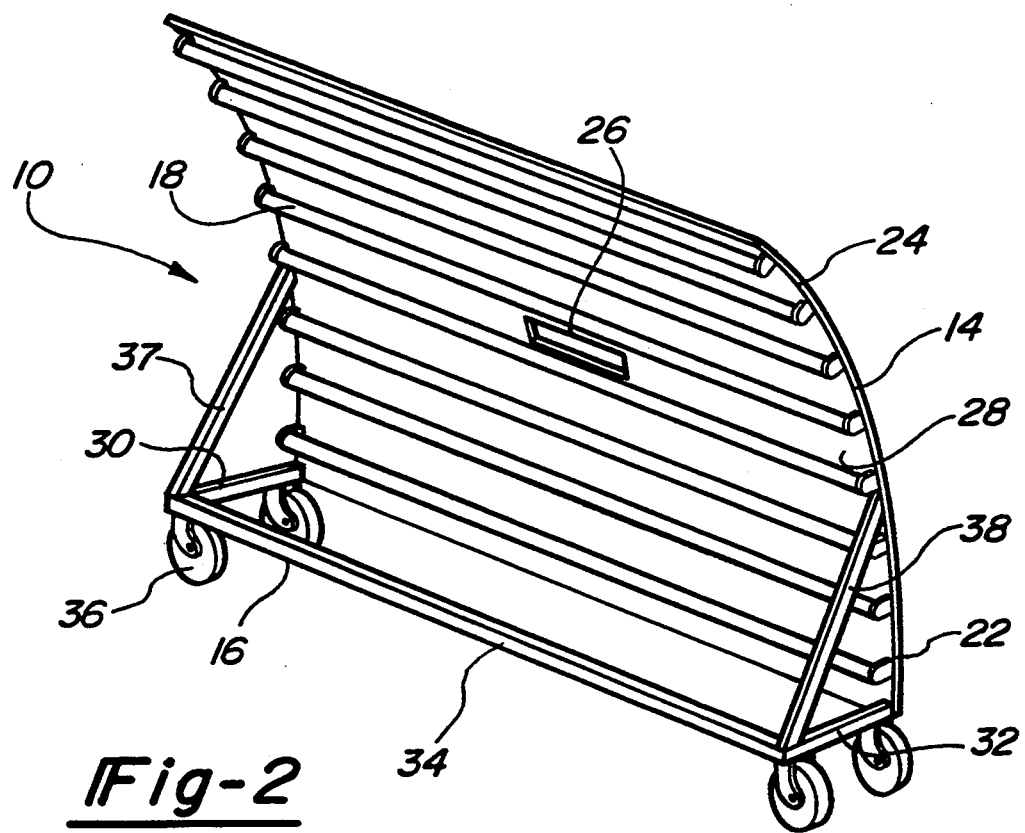
FIG. 2 is a front perspective view of the apparatus of FIG. 1.
Figure 3:
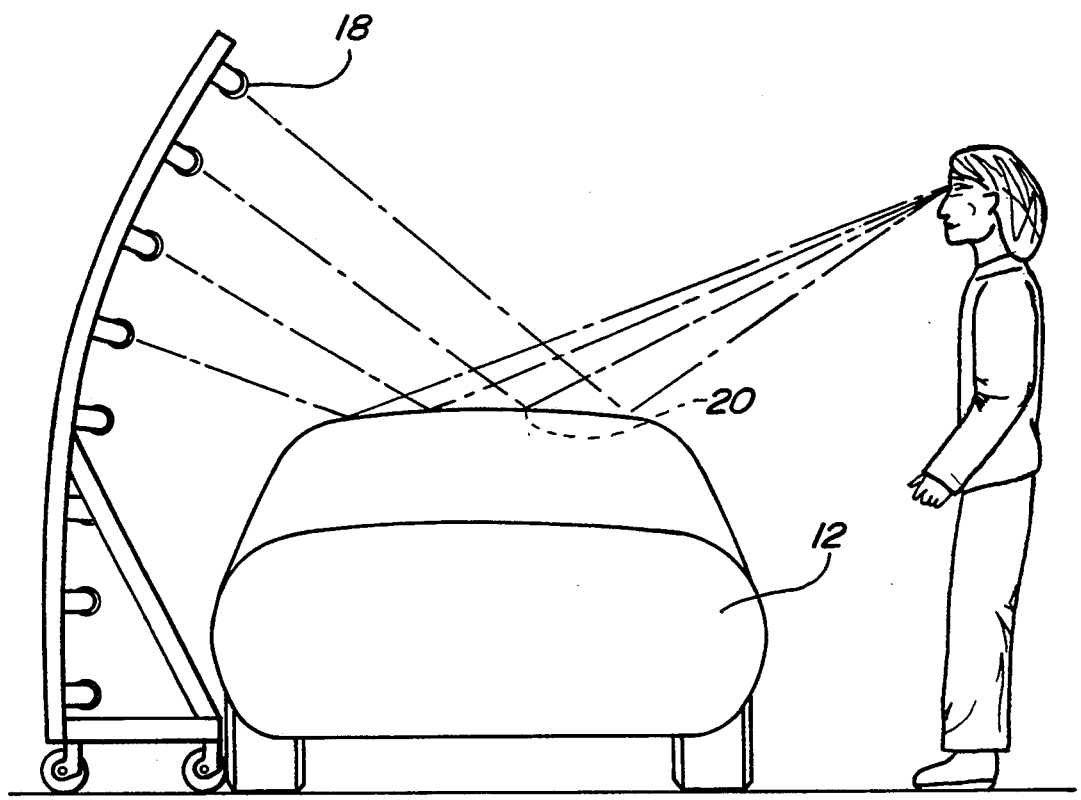
FIG. 3 is a side elevation view of the apparatus of FIG. 1, shown in operative association with a vehicle model.

Turning to FIGS. 1-3, illustrated is a first embodiment of the apparatus 10 of the present invention for inspecting a reflective object. In FIGS. 1 and 3, the apparatus is shown associated with a clay vehicle verification model 12. It will be appreciated by those skilled in the art that the teachings of the present invention are applicable to a wide range of applications and the illustrated application is merely exemplary.

The apparatus 10 of the first embodiment is particularly applicable for inspecting a reflective object, such as a vehicle verification model 12. Preferably, the apparatus 10 comprises a main body member 14, a base portion 16, and light-emitting means 18 for producing at least one elongated image 20 on the reflective object 12.

The main body member 14 includes a lower portion 22 and an upper portion 24. The lower portion 22 is generally linear, and disposed substantially vertical. The upper portion 24, which is integral with the lower portion 22, is concavely curved in the front view. Preferably, the upper portion 24 has a constant radius of curvature of approximately 76 inches. The upper portion 24 begins at a distance of approximately 42 inches from the ground and continues to a maximum vertical height of approximately 9 feet. The upper portion 24 includes an aperture 26 through which one vantage point is provided for evaluating the reflective object 12. A flap (not shown) can be positioned so as to cover the aperture 26 when not in use. Further in the preferred embodiment, the front side 28 of the main body member 14 is coated with flat black paint, thereby maximizing the contrast between the light-emitting means 18 and the remainder of the apparatus 10.

The base portion 16 of the apparatus 10 is constructed of square steel tubing. In this regard, the base portion 16 includes first and second sides 30, 32, and a front side 34. The first and second sides 32, 34 are preferably each attached at one end directly to the main body member 14, and at the other end to the front side 34. A pair of casters 36 are disposed on the bottoms of each of the first and second sides 30, 32. The base portion 16 further includes first and second support arms 37, 38 which upwardly extend from the front corners of base portion 16 to attach to the main body member 14.

In the preferred embodiment, the light-emitting means for producing at least one elongated image on the reflective object comprises a plurality of elongated fluorescent tubes 18. The apparatus 10 is electrically adapted, as is well known in the art, to readily accept commercially available fluorescent bulbs 18. In the exemplary embodiment, the apparatus 10 includes eight (8) such tubes 18 which are 8 feet in length. The fluorescent tubes 18 are horizontally disposed and equally spaced. It will be appreciated by those skilled in the art, that a housing (not shown) can be mounted on the base portion 16 which is adapted to retractably store an extension cord in electrical communication with the tubes 18.

Referring particularly to FIG. 3, the operation of the apparatus 10 of the first embodiment will be described in greater detail. The apparatus 10 is designed to be situated in close proximity to the object 12 to be evaluated. Depending on the particular vantage point desired by the observer, the apparatus 10 can be positioned immediately adjacent the object 12 (as shown in FIG. 3), or a few feet from the object 12. The casters 36 provided on the base portion 16 of the apparatus 10 allow the apparatus 10 to be easily positioned about the object 12 without having to move the object 12.

Where the surface of the reflective object 12 is smooth, the fluorescent tubes 18 produce straight or smoothly curving, uninterrupted images in the object. (See for example FIG. 1) However, a flawed surface produces images having portions with discontinuous curvature. An example of such a flaw is illustrated in FIG. 1 and generally identified with reference numeral 40.

According to the general laws of wave transmission, the light rays emitted from the apparatus 10 create an equal angle of incidence and angle of reflection $\alpha$ and angle of refraction $\beta$ with respect to the surface of the reflective object 12. Thus, the curvature of the upper portion 24 is provided so as to create a substantially equal spacing of the images in the "roof" of the reflective object 12. FIG. 1 illustrates the images formed in the windshield portion and hood portion of the vehicle-like object 12 as would be seen from the vantage point illustrated in FIG. 3. While FIG. 3 illustrates the light rays reflecting off of the roof of the vehicle-like object 12 it will be understood that other surfaces such as the hood, trunk, side plane, door fenders, and quarter panels, among others, can be viewed in the described manner from the vantage point shown in FIG. 3 or from alternative vantage points.

Figure 4:
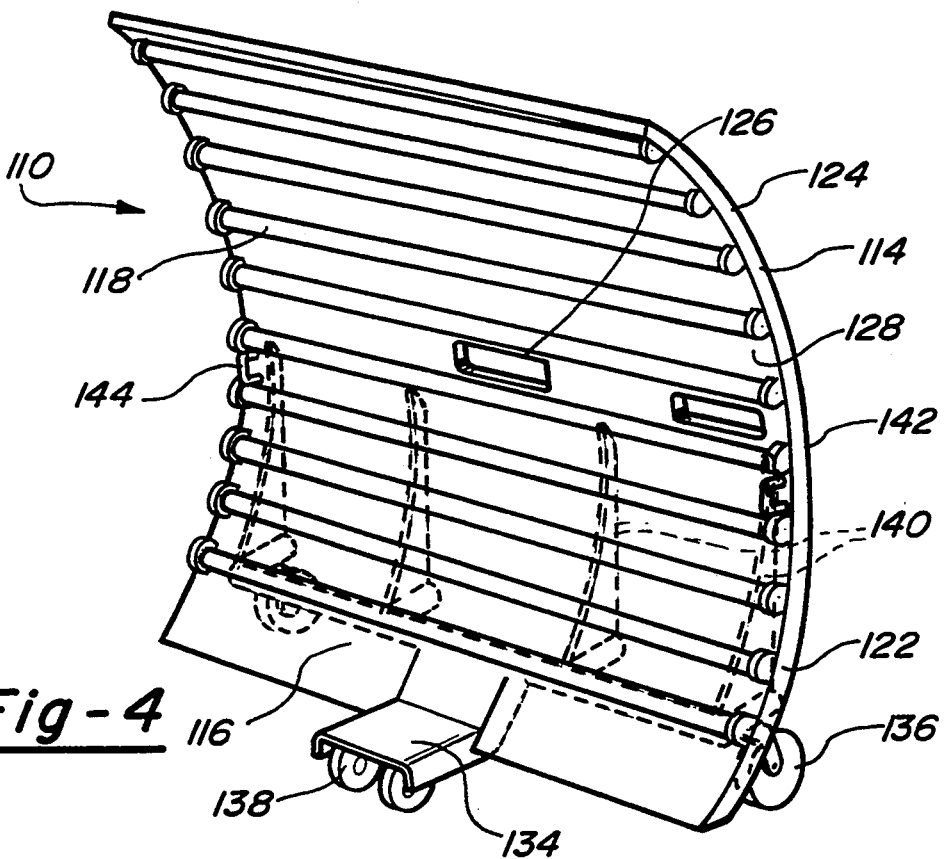
FIG. 4 is a side elevation view of a second embodiment of an apparatus incorporating the teachings of the present invention, shown in operative association with a vehicle model.

Referring to FIGS. 4 and 5 a second preferred embodiment according to the teachings of the present invention is provided. Under this embodiment the apparatus 110 for inspecting reflective objects such as a clay verification model 112 includes a main body member 114, a base portion 116 and a light-emitting means 118. The main body member 114 includes a lower portion 122 and a upper portion 124. Unlike the embodiment illustrated in FIGS. 1 through 3 the lower portion 122 is concavely curved toward the object to be inspected similar to the upper portion 124. Ideally, the body member 114 will have a constant radius of curvature of at least 76 inches as measured from the lower edge of the lower portion 122 up to the top edge of the upper portion 124. Again, the upper portion 124 begins at a distance of approximately 42 inches from the ground and continues to a maximum vertical height of approximately 9 feet.

At least one aperture 126 is disposed along the main body member 114 slightly above the point where the upper portion 124 begins, thereby providing an additional vantage point through for an individual utilizing the apparatus to view the reflective object 112 for evaluation. While this aperture 126 is preferably provided at this centrally located position, it will be understood by those skilled in the art that more than one aperture can be provided along the body member 114, at differing points.

Preferably, the front side 128 of the main body member 114 is coated with a flat black paint, thereby maximizing the contrast between the light emitting means 118 and the remainder of the apparatus 110.

As illustrated in FIGS. 3 and 4 the base portion 116 includes a leg 134 extending forward beyond the base portion 116 to assist in balancing the apparatus 110. Ideally, the leg 134 is provided with wheels 138. Similar to the first embodiment a pair of castors 136 are disposed along the bottoms of each of the first and second ends to assist in transporting the apparatus to various locations about the reflective object 12.

Also, disposed along the back side 142 of the apparatus 110 are a plurality of gussets 140 which are attached to both the back side 142 and the base portion 116 to provide the apparatus with additional structural integrity. Preferably, a pair of handles 144 are provided along each end 130 and 132, respectively, of the apparatus to assist in transporting the apparatus 110 about the reflective object 12.

Under this second preferred embodiment, the light emitting means 118 for producing the at least one elongated image 120 on the reflective object 12 comprises a plurality of spaced apart horizontally oriented elongated fluorescent tubes 118. Although the light-emitting means are preferably fluorescent tubes 118 as shown, it will be appreciated by those skilled in the art that any suitable light-emitting means capable of reflecting off of the object 12 may be employed. For example, electroluminescent lighting (not shown) is such a suitable source of light. A third embodiment incorporating electroluminescent lighting is shown in FIGS. 6 and 7.

Electroluminescent devices in general have a characteristic as a plane light source of low power consumption. As is known by those skilled in the art, the light-emitting body of an electroluminescent device is a thin layer formed of a composition comprising a dielectric material at the matrix and a particulate electroluminescent material, such as zinc sulfide, zinc selenide, zinc silicate, boron nitride, silicon carbide and the like, uniformly disbursed in the matrix. It is also known that the brightness of the electroluminescent layer depends on the dielectric constant of the dielectric material as the matrix and a dielectric material having a larger dielectric constant gives a higher brightness. A conventional electroluminescent light source has a transparent front face behind which are located layers of a transparent electrode, a phosphor, a control resistor and another electrode which need not be transparent. The complete device is commonly encapsulated to protect the device layers from physical or chemical damage.

The application of a voltage to the electrodes of the device induces a flow of electrons from one electrode to the other via the phosphor layer and the control resistor. It is usual for the voltage to be applied such that the transparent electrode acts as a cathode while the second electrode forms the anode; electrons thus flow from the transparent electron through the phosphor and control layers, to the second electrode. Interaction of these electrons with the phosphor causes light to be emitted.

The apparatus 200 for the inspection of a reflective surface of the third embodiment of the present invention includes a main body portion 202 constructed of light-weight foam, thereby minimizing the overall weight. Preferably, the length of the main body portion 202 is approximately 4 feet and the width 20 inches.

The apparatus 200 of the third embodiment further includes a rear side 204 and a front side 206. The rear side 204 is unitarily molded to include first and second handle members 208, 210 provided to assist a user in holding and steadying the apparatus 200. The rear side 204 and front side 206 of the apparatus 200 cooperate to define a cavity (not shown) adapted to contain a power source (not shown). As will be appreciated by those skilled in the art, the light source of the alternative embodiment could also be powered by other power sources, such as a belt pack.

The light-emitting means of the third embodiment comprises a plurality of electroluminescent strips 212. In the exemplary embodiment illustrated, the apparatus 200 includes three (3) electroluminescent strips 212 which are 12 mm wide and 175 mm apart. The electroluminescent strips 212 are mounted in the front side 206 of the main body portion 202.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. An apparatus for visually evaluating a plurality of surfaces of a three dimensional vehicle-like object having a reflective exterior, said apparatus comprising:
    a main body portion including an upper portion and a lower portion, said upper portion including a concavely curved inner surface; and
    a plurality of horizontally disposed light emitting members attached to said main body portion along both said upper and lower portions for producing multiple elongated images on said three dimensional vehicle-like object, said multiple elongated images including at least one elongated image in a portion of a first surface of said three dimensional vehicle-like object and at least one elongated image in a portion of a second surface of said three dimensional vehicle-like object;
    said apparatus is movable and positionable about said three dimensional vehicle-like object.

2. The apparatus of claim 1, wherein each of said plurality of horizontally disposed light emitting members comprises an elongated light bulb.

3. The apparatus of claim 2, wherein a first elongated light bulb is attached to said upper portion of said main body member and a second elongated light bulb is attached to said lower portion of said main body member.

4. The apparatus of claim 2, wherein said elongated light bulbs are equally spaced apart.

5. The apparatus of claim 1, further comprising a base portion attached to a lower edge of said lower portion, said base portion including a plurality of casters.

6. The apparatus of claim 1, wherein said concavely curved inner surface has a radius of curvature of at least approximately 76 inches.

7. The apparatus of claim 1, wherein said lower portion includes a concavely curved inner surface.

8. An apparatus for visually evaluating a plurality of surfaces of a three dimensional vehicle-like object having a reflective exterior, said apparatus comprising:
    a portable main body portion including a lower portion having a lower inner surface extending in a substantially vertical direction and an upper portion having an upper inner surface extending in a vertical and lateral direction following an arc, said portable main body being movable about the three dimensional vehicle-like object;
    a first light emitting member horizontally disposed on the lower portion for producing a first elongated image on a first surface of the three dimensional vehicle-like object; and
    a second light emitting member horizontally disposed on the upper portion for producing a second elongated image on a second surface of the three dimensional vehicle-like object.

9. The apparatus of claim 8, further comprising a base portion attached along a lower edge of said lower portion, said base portion including a plurality of casters.

10. The apparatus of claim 8, wherein the first and second light emitting members comprise elongated light bulbs.

11. The apparatus of claim 8, wherein the first and second light emitting members comprise elongated electroluminescent lighting.

12. The apparatus of claim 8, further comprising at least two light emitting members being equally spaced on the lower portion and at least two light emitting members being horizontally disposed and equally spaced on the upper portion.

13. The apparatus of claim 8, wherein said lower inner surface also extends in a lateral direction.

14. An apparatus for visually evaluating a plurality of surfaces of a three dimensional vehicle-like object having a reflective exterior, said apparatus comprising:
- a portable main body portion including a lower portion having a substantially vertical inner surface, an upper portion integral with the lower portion and having a concavely curved inner surface and a base portion attached to the lower portion having a plurality of casters attached thereto;
- a plurality of horizontally disposed, equally spaced light emitting members attached to the lower portion along both said upper and lower portions for producing a plurality of elongated images on a first, substantially vertical surface of the three dimensional vehicle-like object; and
- a plurality of horizontally disposed, equally spaced light emitting members attached to the concavely curved inner surface of the upper portion for producing a plurality of elongated images on a second substantially horizontal surface of the three dimensional vehicle-like object.

15. An apparatus for visually evaluating a plurality of surfaces of a three dimensional vehicle-like object having a reflective exterior, said apparatus comprising:
- a portable main body portion including a lower portion having a concavely curved inner surface, an upper portion integral with the lower portion having a concavely curved inner surface following an arc, said portable main body being movable about the three dimensional vehicle-like object, and a base portion attached to the lower portion having a plurality of casters attached thereto;
- a plurality of horizontally disposed, equally spaced light emitting members attached to the concavely curved inner surface of the lower portion for producing a plurality of elongated images on a first, substantially surface of the three dimensional vehicle-like object; and
- a plurality of horizontally disposed, equally spaced light emitting members attached to the concavely curved inner surface of the upper portion for producing a plurality of elongated images on a second surface of the three dimensional vehicle-like object.

* * * * *